United States Patent [19]

Staudenmaier et al.

[11] Patent Number: 5,663,329

[45] Date of Patent: Sep. 2, 1997

[54] PREPARATION OF ENANTIOMERICALLY PURE LACTAMS

[75] Inventors: Horst Ralf Staudenmaier, Birkenheide; Bernhard Hauer, Fussgönheim; Friedhelm Balkenhohl, Limburgerhof; Wolfgang Ladner, Fussgönheim; Ursula Schnell, Bad Lippspringe; Uwe Pressler, Waldsee, all of Germany

[73] Assignee: BASF Aktiengesellschaft, Ludwigshafen, Germany

[21] Appl. No.: 641,773

[22] Filed: Apr. 30, 1996

Related U.S. Application Data

[63] Continuation of Ser. No. 470,048, Jun. 6, 1995, abandoned.

[30] Foreign Application Priority Data

Jun. 15, 1994 [DE] Germany ................ 44 20 751.4

[51] Int. Cl.$^6$ .............. C07D 205/08; C07D 201/02; C07D 211/88; C07D 207/26
[52] U.S. Cl. .............. 540/200; 540/540; 540/362; 546/243; 548/543
[58] Field of Search .............. 540/200, 540, 540/362; 546/243; 548/543

[56] References Cited

U.S. PATENT DOCUMENTS 3,770,585  11/1973  Fukumura ................. 195/29
5,284,769   2/1994  Evans et al. ............. 435/280

FOREIGN PATENT DOCUMENTS 424 064    10/1989  European Pat. Off. .
357 029     3/1990  European Pat. Off. .
21 57 171  11/1971  Germany .

*Primary Examiner*—Mukund J. Shah
*Assistant Examiner*—Bruck Kifle
*Attorney, Agent, or Firm*—Keil & Weinkauf

[57] ABSTRACT

A process for preparing enantiomerically pure lactams of the formula I

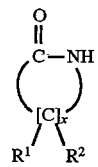

where

R$^1$ and R$^2$ are each, independently of one another, H, unsubstituted or substituted C$_1$–C$_4$-alkyl, unsubstituted or substituted C$_2$–C$_4$-alkenyl, unsubstituted or substituted aryl, (CH$_2$)$_n$—COOH with n=0, 1, 2, 3, and X is 1, 2, 3, 4, 5, from a racemate of the formula I by. allowing a biocatalyst which selectively converts one enantiomer from I to act on the racemic mixture of I, and isolating the unconverted enantiomer from the resulting mixture of products.

7 Claims, No Drawings

PREPARATION OF ENANTIOMERICALLY PURE LACTAMS

This application is as continuation of application Ser. No. 08/470,048, filed on Jun. 6, 1995, now abandoned.

The present invention relates to a process for preparing enantiomerically pure lactams of the formula I

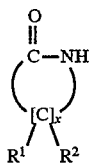

where $R^1$ and $R^2$ are each, independently of one another, H, unsubstituted or substituted $C_1$–$C_4$-alkyl, unsubstituted or substituted $C_2$–$C_4$-alkenyl, unsubstituted or substituted aryl, $(CH_2)_n$—COOH with n=0, 1, 2, 3, and X is 1, 2, 3, 4, 5.

EP 424 064 describes the stereoselective cleavage of lactams with the aid of microorganisms. This process makes use of two different microorganisms each of which hydrolyzes one enantiomer to the corresponding amino acid. However, the disadvantage of this process is that it is confined to certain bicyclic lactams as substrate and therefore is not amenable to wide use.

In addition, DE 21 57 171 discloses a process with which it is possible to prepare optically pure lysine from racemic α-amino-ε-caprolactam. The substrate spectrum of the strains used in this case, and of the enzyme L-α-amino-ε-caprolactam hydrolase isolated from these strains, is extremely narrow, however. Thus, it is expressly stated therein that even compounds with a very similar structure, such as ε-caprolactam, δ-valerolactam, α-butyrolactam, cyclic oligomers of ε-aminocaproic acid or D- and L-pyrrolidonecarboxylic acid, are not hydrolyzed (DE 21 57 171, page 18, Substrate specificity). The only exception to this rule is the conversion of α-amino-substituted δ-valerolactams which are described in EP 357 029 and by T. Fukumura in Plant & Cell Physiol. 18 (1977) 1173–1176. This process is therefore also unsuitable for wide use and can, on the contrary, be used only for the said reactions.

It is an object of the present invention to provide a process for preparing enantiomerically pure lactams which does not have the structural limitations described above and with which it is possible to prepare enantiomerically pure lactams with the formula I in good yield.

We have found that this object is achieved by a process for preparing enantiomerically pure lactams of the formula I

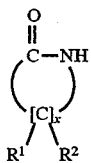

where $R^1$ and $R^2$ are each, independently of one another, H, unsubstituted or substituted $C_1$–$C_4$-alkyl, unsubstituted or substituted $C_2$–$C_4$-alkenyl, unsubstituted or substituted aryl, $(CH_2)_n$—COOH with n=0, 1, 2, 3, and X is 1, 2, 3, 4, 5, from a racemate of the formula I by allowing a biocatalyst which selectively converts one enantiomer from I to act on the racemic mixture of I, and isolating the unconverted enantiomer from the resulting mixture of products.

The racemic lactams of the formula I preferably employed in the process according to the invention are those which have a ring size of 4, 5 or 6 carbon atoms (X=2, 3 or 4) and in which all the substituents $R^1$ and $R^2$ apart from one have the meaning H, while the single substituent has one of the abovementioned meanings.

The lactams which are particularly preferred among these are those in which the single substituent $R^1$ which is different from H is methyl or vinyl.

Suitable microorganisms as biocatalysts for the process according to the invention are those which have the property of converting only one enantiomer of the compounds defined by formula I, while they leave the other enantiomer unaffected. Microorganisms of this type can easily be isolated by conventional processes, for example from soil samples, and one of these processes is described in Example 1.

Preferred microorganisms are fungi and bacteria. Those of the genera Pseudomonas and Rhodococcus are particularly preferred.

The following strains have been deposited at the Deutsche Sammlung für Mikroorganismen und Zellkulturen GmbH, DSM, on Feb. 28, 1994, as representatives of organisms which selectively hydrolyze one or other of the enantiomers:

Lu 8676 (*Rhodococcus erythropolis*): DSM 9002 and
Lu 8745 (*Pseudomonas aeruginosa*): DSM 9001.

The enantioselectivity of these deposited strains is described in detail in the following Examples.

Another suitable microorganism is Lu 8744 which has been classified as *Pseudomonas aeruginosa*.

For the stereoselective cleavage of a lactam it is in principle only necessary to have an enzyme which cleaves one enantiomer to the corresponding amino acid while it leaves the other enantiomer unaffected. For this reason it is possible to use as biocatalyst for the process according to the invention apart from whole microorganisms also enzymatic extracts thereof or isolated enzymes.

The biocatalysts can be employed as such or in immobilized form, eg. carrier-bound.

Once the biocatalyst has selectively hydrolyzed one enantiomer of the racemate, the mixture of products comprises one enantiomer of the amino acid and one enantiomer of the lactam.

A mixture of products of this type can easily be fractionated by conventional processes on the basis of the different physicochemical properties of the components.

Suitable examples are distillation, extraction, crystallization or chromatographic processes such as ion exchange chromatography.

Moreover, in many cases only the enantiomer of the unconverted lactam is still detectable, the other enantiomer having apparently been degraded further.

The reaction of the biocatalyst with the racemate normally takes place at from 0 to 50, preferably from 20° to 40, °C.

If whole microorganisms are employed as biocatalysts, the conversion is preferably carried out in a nutrient medium to which the lactams to be converted are added.

The lactam concentration in the nutrient solution is, as a rule, from 1 to 100 g of lactam per liter of nutrient solution.

If enzyme extracts or enzymes purified from the corresponding microorganisms are employed as biocatalysts, it is advisable to carry out the conversion of the racemates in aqueous solution or in organic solvents or mixtures of these two.

The conversion is advantageously carried out at a pH at which the biocatalysts still have high activity. This is, as a rule, the case at a pH of from 3 to 9, preferably from 4 to 8.

The process according to the invention is particularly suitable for preparing enantiomerically pure substituted 2-pyrrolidinones, for example methyl- or vinyl-substituted 2-pyrrolidinones.

The process according to the invention has few limitations in respect of structural parameters of the lactams to be converted, such as ring size or nature and position of the substituent.

The invention furthermore relates to the isolation of that enantiomer which has been converted by the biocatalyst and to the use thereof as such or after conversion back into the lactam.

If, for example, the (S) form of a lactam is selectively hydrolyzed by the biocatalyst, the (R) form of the lactam remains unchanged and can be isolated directly from the mixture.

The hydrolyzed (S) form, which is then present as the corresponding enantiomerically pure amino acid, can be used as such or after cyclization to the (S)-lactam.

The enantiomerically pure lactams are valuable intermediates for active substances in the drugs and crop protection sectors. The invention is explained further by the following examples.

EXAMPLE 1

Isolation of Strains with Stereoselective Lactamase Activity from Soil Samples

About 2 g of each soil sample were placed in an Erlenmeyer flask containing 30 ml of lactamase medium with 2 g/l of a lactam, eg. pyrrolidone, and incubated with shaking at 25° C. for 2–7 days.

Lactamase Medium:

| | |
|---|---|
| $MgSO_4 \times 7H_2O$ | 0.5 g/l |
| NaCl | 0.05 g/l |
| $CaCl_2$ | 0.02 g/l |
| Trace element solution | 2 ml/l |
| $KH_2PO_4$ | 1.5 g/l |
| $K_2HPO_4$ | 3.6 g/l |
| Glycerol | 5 g/l |

Trace element solution
  200 mg/l iron(II) sulfate 1-hydrate
  10 mg/l zinc(II) sulfate 4-hydrate
  3 mg/l Manganese chloride 4-hydrate
  30 mg/l boric acid
  20 mg/l cobalt(II) chloride 6-hydrate
  1 mg/l copper(II) chloride 2-hydrate
  2 mg/l nickel(II) chloride 6-hydrate
  3 mg/l sodium molybdate 2-hydrate
  500 mg/l ethylenediaminetetraacetic acid (EDTA)

To enrich suitable strains, 1 ml portions of these cultures were transferred into new medium and again shaken for some days, and the same procedure was repeated once again. The cultures were then plated out on agar plates with the same composition as the enrichment medium. Single colonies were removed from these plates and were tested:

The strains were cultured in lactamase medium with 5 g/l of the racemic lactam 5-vinylpyrrolidinone for 2–7 days. A sample was taken each day and tested for formation of an optically active product:

3 ml of ethyl acetate were added to 3 ml of culture, vigorously mixed and centrifuged to separate the phases. After filtration through a 0.2 μm filter, the ethyl acetate extract was used directly for measurement of the rotation in a polarimeter.

This screening resulted in isolation of a total of 5 strains which formed an optically active product. 2 strains produced dextrorotatory 5-vinylpyrrolidinone and 3 strains produced levorotatory 5-vinylpyrrolidinone.

Strains were cultivated in a similar way in lactamase medium with 5 g/l of the racemic lactam 3-methylpyrrolidinone and were investigated. 2 strains which produced dextrorotatory 3-methylpyrrolidinone were isolated.

EXAMPLE 2

(S)-5-Vinylpyrrolidinone from (R,S)-5-vinylpyrrolidinone 25 ml of lactamase medium containing 5 g/l 5-vinylpyrrolidinone were inoculated with DSM 9002 and shaken at 30° C. for 4 days. This preculture was used to inoculate 500 ml of the same mediumas the main culture, which was incubated with shaking for 5 days.

The cells were removed by centrifugation, and the cell-free supernatant was extracted with ethyl acetate continuously for 12 h. The solvent was removed from the ethyl acetate extract to afford a residue of 1.43 g of 5-vinylpyrrolidinone. The structure of the isolated product was confirmed by NMR.

The following rotations were determined for the product:

$[\alpha]_D = +27.0$ (c=1, ethyl acetate)

$[\alpha]_D = +45.3$ (c=1, ethanol)

Comparison of the rotation with literature data (GB 21 33 002, Example 10) showed that the product is the S enantiomer.

The enantiomer ratio was determined by chiral GC and showed an enantiomeric excess ee of 98.6% (column: Cyclodex-β-I/P, 50 m×0.32 mm).

The enantiomer was obtained in high yield. Small amounts of organic components were also isolated by the ethyl acetate extraction but are easily removable.

EXAMPLE 3

(R)-5-Vinylpyrrolidinone from (R,S)-5-vinylpyrrolidinone 500 ml of lactamase medium containing 2 g/l pyrrolidone were inoculated with DSM 9001 and shaken at 30° C. for 2 days. Then 2.5 g of racemic 5-vinylpyrrolidinone were added and the culture was shaken for a further 5 days. The culture was stopped and worked up as in Example 2. A residue of 0.82 g of (R)-5-vinylpyrrolidinone was obtained.

The product had a rotation of $[\alpha]_D = -27.7$ (c=1, ethyl acetate).

EXAMPLE 4

Stereoselective Conversion of Various Lactams and Amides

The strains from Example 1 were cultivated in lactamase medium with 5 g/l of one of the compounds listed in Table 1 for 2–7 days. Samples were taken from the cultures at intervals of 1–2 days and tested for formation of an optically active product. The samples were obtained as in Example 1.

TABLE

| Substrate | Strain | |
|---|---|---|
| | Levorotatory product | Dextrorotatory product |
| 5-Vinylpyrrolidinone | Lu 8744, 8745, 8746 | Lu 8676, 8743 |
| 3-Methylpyrrolidinone | Lu 8744, 8746 | Lu 8747, 8748 |
| 6-Phenylvalerolactam | Lu 8744, 8745, 8746 | |

We claim:

1. A process for preparing enantiomerically pure lactams of the formula I

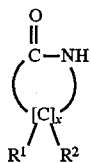

where

R$^1$ and R$^2$ are each, independently of one another, H, unsubstituted or substituted C$_1$–C$_4$-alkyl, unsubstituted or substituted C$_2$–C$_4$-alkenyl, unsubstituted or substituted aryl, and (CH$_2$)$_n$—COOH with n=0, 1, 2, 3, and X is 1, 2, 3, 4, 5, from a racemate of the formula I by allowing a bacterium which selectively converts one enantiomer from I to act on the racemic mixture of I, and isolating the unconverted enantiomer from the resulting mixture of products.

2. The process of claim 1, wherein the bacterium is a microorganism of the genus Rhodococcus or Pseudomonas.

3. The process of claim 1, wherein an (S)-enantiomer of I is prepared using *Rhodococcus erythropolis* DSM 9002 as bacterium.

4. The process of claim 1, wherein an (R) enantiomer of I is prepared using *Pseudomonas aeruginosa* DSM 9001 as bacterium.

5. The process of claim 3, wherein (S)-5-vinylpyrrolidinone is prepared.

6. The process of claim 4, wherein (R)-5-vinylpyrrolidinone is prepared.

7. The process of claim 1, wherein a enzymatic extract of the bacterium is used.

* * * * *